(12) United States Patent
Ando et al.

(10) Patent No.: US 8,148,505 B2
(45) Date of Patent: Apr. 3, 2012

(54) METHOD OF α-SELECTIVE GLYCOSYLATION

(75) Inventors: Hiromune Ando, Gifu (JP); Akihiro Imamura, Gifu (JP); Makoto Kiso, Gifu (JP); Hideharu Ishida, Gifu (JP)

(73) Assignee: Japan Science and Technology Agency, Saitama (JP)

( * ) Notice: Subject to any disclaimer, the term of this patent is extended or adjusted under 35 U.S.C. 154(b) by 356 days.

(21) Appl. No.: 10/555,565

(22) PCT Filed: May 19, 2004

(86) PCT No.: PCT/JP2004/007155
§ 371 (c)(1),
(2), (4) Date: Dec. 1, 2005

(87) PCT Pub. No.: WO2004/104163
PCT Pub. Date: Dec. 2, 2004

(65) Prior Publication Data
US 2006/0122379 A1    Jun. 8, 2006

(30) Foreign Application Priority Data

May 22, 2003   (JP) .................................. 2003-144622

(51) Int. Cl.
*C07G 3/00*   (2006.01)
*C07H 17/00*  (2006.01)

(52) U.S. Cl. ...................................................... 536/18.5

(58) Field of Classification Search ........................ None
See application file for complete search history.

(56) References Cited

U.S. PATENT DOCUMENTS 5,371,210 A    12/1994   Chou
5,837,830 A *  11/1998   Koganty et al. .............. 536/17.9

FOREIGN PATENT DOCUMENTS

| JP | 5-70471 | 3/1993 |
| JP | 6-157570 | 6/1994 |
| JP | 9-286793 | 11/1997 |

OTHER PUBLICATIONS

Lear et al. Angew. Chem. Int. Ed. 2001, 40, No. 5, 946-949.*
Chen et al. Tetrahedron Letters 44 (2003) 3691-3695.*
Plante et al. Organic Letters, vol. 2, No. 24, 2000, 3841-3843.*
Imamura et al. Tetrahedron Letters 44 (2003) 6725-6728.*
Yeung et al. Organic Letters 2000, vol. 2, No. 9, 1279-1282.*
Yoshizaki et al. (Angew. Chem. Int. Ed. 2001, 40, No. 8, pp. 1475-1480.*
Paulsen et al.; Synthese der Trisaccharidkette der Determinante der Blutgruppensubstanz A, Typ 1; Chem. Ber. 111, pp. 2370-2375, (1978).
Paulsen et al.; Synthese α-glycosidisch verknüpfter Disaccharide der 2-Amino-2-desoxy-D-galactopyranose; Chem. Ber. 111, pp. 2358-2369, (1978).
Lemieux & Latcliffe; Th azidonitration of tri-*O*-acetyl-D-Galactal[1]; National Research Council of Canada, pp. 1244-1251, (1979).
Ferrari & Pavia; The synthesis of derivatives of 3-O-(2-acetamido-2-deoxy-α-D-galactopyranosyl)-L-threonine*;   Carbohydrate Research, pp. C1-C7, (1980).
D. Kumagai et al., "Cyclic di-*t*-butylsilylenediyl Ether Group as a Convenient Protective Group for the Glycoconjugate Synthesis," Tetrahedron Letters 42 (2001) 1953-1956.

* cited by examiner

*Primary Examiner* — Layla Bland
(74) *Attorney, Agent, or Firm* — Jordan and Hamburg LLP (57) ABSTRACT

An α-selective glycosylation process of a glycosylation reaction between a sugar structure of hexose or an aldose having a chain with six or more carbon atoms in the molecule, which is a monosaccharide or a reducing end of an oligosaccharide with two or more monosaccharide residues connected by glycosidic linkages (an oligosaccharide with two monosaccharide residues is disaccharide) (also referred to as "a disaccharide to an oligosaccharide") or a sugar chain and alcoholic hydroxyl group or thiol group, to obtain a sugar structure glycoside containing α-glycoside at a high ratio, under the ring-shaped formation of a protective group in a silyl acetal structure over hydroxyl groups at positions 4 and 6 in the sugar structure.

By the process, highly selective α-glycosylation of sugar structure can be progressed in a simple and efficient manner.

25 Claims, 3 Drawing Sheets

METHOD OF α-SELECTIVE GLYCOSYLATION

TECHNICAL FIELD

The present invention relates to an α-selective glycosylation process. More specifically, the invention relates to an α-selective glycosylation process of sugar structures with galactose and other given essential structures, and derivative compounds thereof, or oligosaccharides with two or more monosaccharide residues connected by glycosidic linkages (oligosaccharide with two monosaccharide residues is disaccharide) (referred to as "disaccharides to oligosaccharides" hereinbelow) or sugar chains, having these sugar structures and derivative compounds thereof at their reducing ends.

BACKGROUND ART

In recent years, particularly in the post-genome era, sugar chain-containing polymers existing as intracellular and extracellular membrane constituents and extracellular molecules in multi-cellular biological organisms, particularly higher biological organisms have drawn attention in relation with the functions thereof in such biological organisms. One typical example of the sugar chain-containing polymers is glycoprotein.

With some exceptions, most of cellular surface membranes and serum proteins in many animals primarily including humans are glycoproteins. For example, antibodies, receptors, hormones and enzymes are not simple proteins but are commonly glycoproteins. The functions of such glycoproteins in biological organisms have traditionally been described from the standpoint of protein structure alone. Since the fact was found that the specificities of ABO (H) type-blood group antigens are determined on the basis of the subtle difference in their sugar chain moieties, however, the roles of sugar chains in glycoproteins as signals have increasingly been focused in relation with various discrimination phenomena required for the establishment and retention of multi-cellular biological organisms.

Specifically, a protein is expressed on the basis of a genetic information and is then glycosylated (added with a sugar chain), to give a biological selectivity extremely specific to the function of the protein itself to the resulting glycoprotein. Glycoproteins are widely distributed in tissues and organisms of animals and plants. Due to the significance of the sugar chains in glycoproteins, diverse and enormous research works have been done and accumulated, for example research works about tumor specific antigens derived from sugar chains. Concurrently, the analysis of sugar chain structures (sequences and steric structures thereof) has made a great progress.

Sugar chains of glycoproteins are broadly classified in N-glycoside linkage type (Asn linkage type) where the sugar chains are linked to L-asparagine as an amino acid residue composing polypeptides and in O-glycoside linkage type (O linkage type) where the sugar chains are linked to L-serine or L-threonine. Among them, sugar chains of O linkage type are found in a wide range including for example various mucous proteins, serum proteins and membrane proteins. Typically, such sugar chains of O linkage type form α-O-glycoside linkage via a nucleophilic reaction using N-acetyl-D-galactosamine as the donor and the alcoholic hydroxyl group of L-serine or L-threonine as the acceptor.

For research works and analyses about the sugar chains of glycoproteins or about lectin drawing attention as a functional protein specifically recognizing the sugar chains of glycoproteins, for example, glycoprotein samples should be prepared at an amount of about several micrograms or more. Because the intended glycoproteins exist at an extremely trace amount in the order of nanogram/milliliter in tissues and cells of animals and plants, generally, the preparation of needed amounts of glycoprotein samples is laborious.

Therefore, research works about the chemical synthesis of glycoproteins of Asn linkage type and O linkage type have been done intensively worldwide. Setting research works about the chemical synthesis of glycoproteins of Asn linkage type aside, various approaches for the chemical synthesis of the glycoproteins of O linkage type have been proposed in terms of O-glycoside linkage very common in the field of sugar chemistry according to techniques developed for the glycosylation of sugar residues together.

The chemical synthesis of glycoproteins of O linkage type involves a very difficult problem as to how the glycosylation between galactosamine at the reducing end and the alcoholic hydroxyl group of amino acid can be facilitated in an α-selective manner. In the glycosylation of N-acetyl-D-galactosamine, in other words, the N-acetylamino group at position 2 interferes with the glycosylation through the neighboring group participation. Accordingly, β-glycosylation also occurs at a considerable ratio, disadvantageously.

Figure 1:
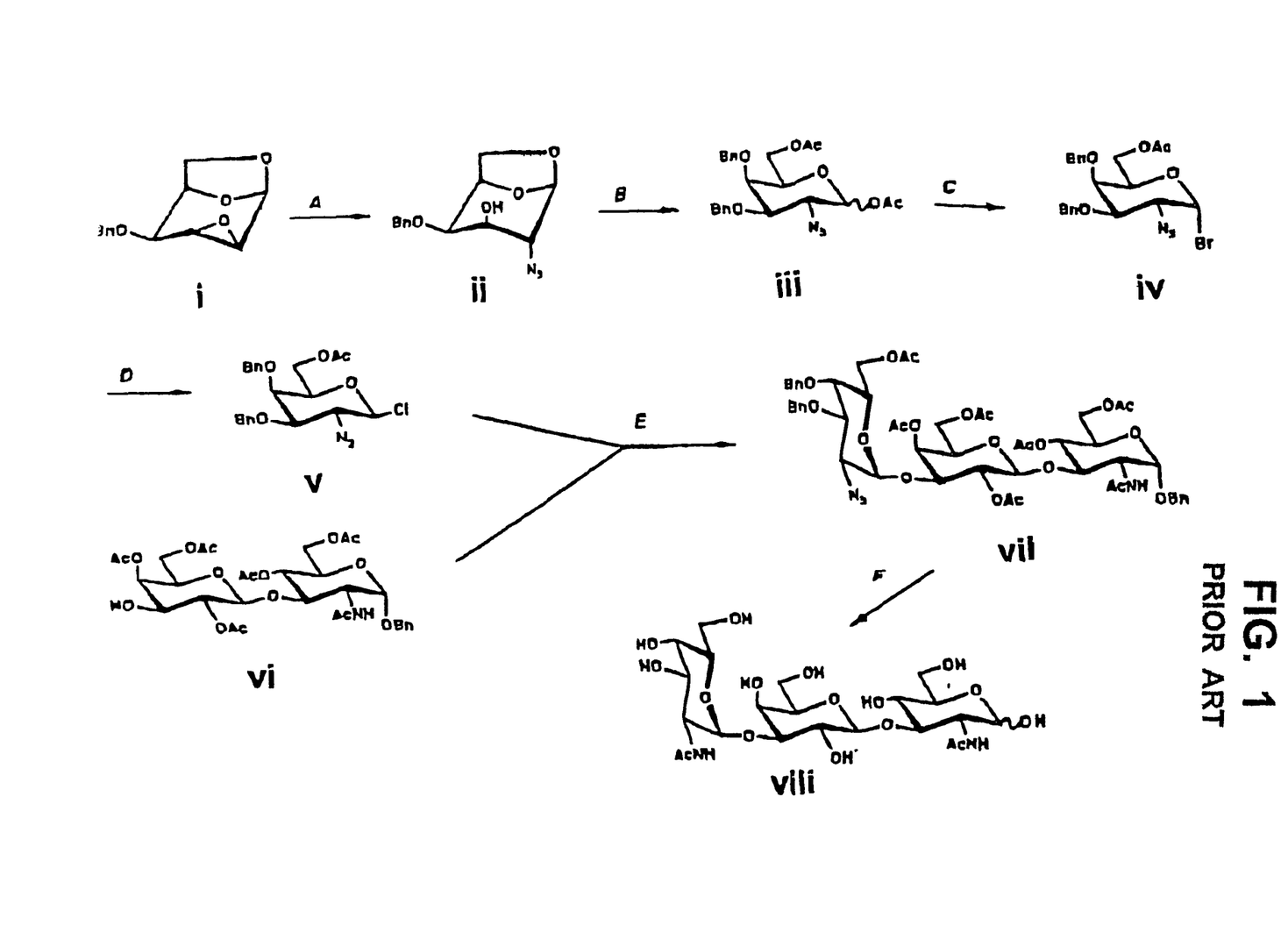
FIG. 1 is a flow chart of an α-selective glycosylation process according to a previous technique.

Paulsen, et al. propose a process using a 2-azide derivative so as to cope with the disadvantage. As shown in FIG. 1, the process includes the stereo-specific cleavage of 1,6;2,3-dianhydrosugar (i) with azide anion to prepare 2-azide (ii), the conversion of the resulting 2-azide to synthetically prepare α-bromide (iv), and the treatment of the resulting α-bromide with tetraethylammonium chloride to prepare β-chloride (v), to thereby prepare α-glycoside under the Koenigs-Knorr reaction conditions.

Figure 2:
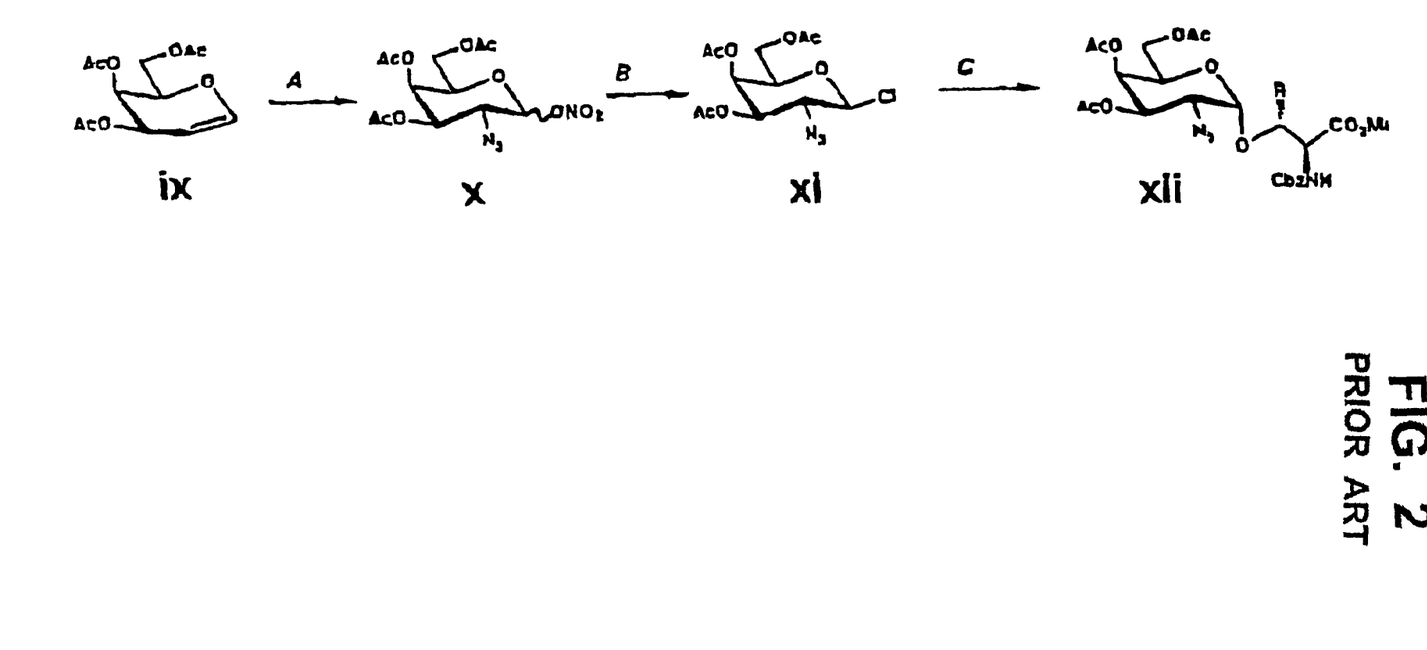
FIG. 2 is a flow chart of an α-selective glycosylation process according to a previous technique.

A simple synthetic process of 2-azide sugar was then developed by Lemieux and Ratcliffe. As shown in FIG. 2, Ferrari and Pavia converted the compound (x) obtained by the synthetic process to β-chloride (xi), which was then condensed with an L-serine derivative, using a mercury salt as a promoter, to obtain α-glycoside (xii) at a yield of 66%.

Furthermore, Paulsen, et al. utilized silver perchlorate and silver carbonate (at a ratio of 1:10) as the promoter in a non-polar mixture solvent of methylene chloride/toluene so as to suppress unnecessary anomerization of the compound (xi) in FIG. 2. The process produced a fruitful result of the yield of 85% and the α selectivity/β selectivity ratio of 19:1.

The various synthetic processes described above, particularly the process of Paulsen, et al. using silver perchlorate and silver carbonate as the promoter produced a very great result from the standpoint of the issue of the (α-selective glycosylation. However, the processes have common disadvantages of poor practical wide applicability in view of donor preparation stage and tough reaction control.

SUMMARY OF THE INVENTION

It is an object of the invention to enable highly selective α-glycosylation of given sugar structures including the chemical synthesis of glycoproteins of O linkage type by a simple and convenient approach.

The present inventors found that highly selective α-glycosylation of sugar chain acceptors could be generated, by simply forming a protective group in a silyl acetal structure on a predetermined hydroxyl group in a sugar structure such as galactose.

In a first aspect of the invention, an α-selective glycosylation process between a sugar structure as a donor and an alcoholic hydroxyl group or thiol group as an acceptor compound, using as the sugar structure a sugar structure of hexose or an aldose having a chain with seven or more carbon atoms in the molecule, which is a monosaccharide or a reducing end of an oligosaccharide with two or more monosaccharide residues connected by glycosidic linkages (oligosaccharide with two monosaccharide residues is disaccharide) (also referred to as "a disaccharide to an oligosaccharide" hereinbelow) or a sugar chain and which should essentially satisfy the constitutional conditions such that the sugar structure has hydroxyl groups at least at positions 4 and 6 and that the hydroxyl group at position 4 is in an axial bond and a group at position 5 is in equatorial bond, comprises the following steps:

(1) a step of forming a protective group in a silyl acetal structure in a ring shape over the hydroxyl groups at positions 4 and 6 in the sugar structure, and (2) a step of promoting the glycosylation between the sugar structure and the alcoholic hydroxyl groups or thiol group, to prepare a sugar structure glycoside containing α-glycoside at a ratio of 80% or more in the ratio of α-/β-glycosides.

According to the α-selective glycosylation process in the first aspect of the invention, highly selective α-glycosylation can be progressed by a very simple approach including the formation of a protective group in a silyl acetal structure in a ring shape over the hydroxyl groups at positions 4 and 6 in a given sugar structure and subsequent glycosylation between the sugar structure and the alcoholic hydroxyl group or thiol group as an acceptor compound. The ratio of α-anomer in the resulting glycoside is generally 80% or more.

At synthetic experiments where the inventors found the effect, 2,2,2-trichloroethoxycarbonyl group (Troc group) and the like existed other than the protective group in the silyl acetal structure in N-acetylgalactosamine as the donor, while the acceptor compound was disialylgalactose. As described below in the following Examples, the inventors verified through sequential verification experiments about these individual elements that the formed protective group in the silyl acetal structure enabled the highly α-selective glycosylation.

As described below, the α-selective glycosylation process is never affected by any interference of N-acetylamino group with glycosylation, which has been a problem in the chemical synthesis of glycoproteins of O linkage type. Compared with the previous techniques proposed from the same standpoint, for example the process using 2-azide derivatives by Paulsen et al. and the modified process of Ferrari and Pavia, the present process is a chemical synthetic process with a practical applicability, only requiring very simple procedures. Therefore, glycoproteins as research samples for the research works and analysis of the sugar chains of glycoproteins, lectin and the like have successfully been prepared by such simple chemical synthesis.

Additionally, the α-selective glycosylation process in the first aspect of the invention can generally been established between a sugar structure (donor) provided with given conditions and an acceptor compound having at least an alcoholic hydroxyl group or thiol group but is never limited to the synthesis of glycoproteins of O linkage type. In other words, the donor may satisfactorily be a monosaccharide or an oligosaccharide while amino acids, peptide chains, monosaccharides, sugar chains and other types of appropriate organic compounds may be used as the acceptor compound as long as these compounds have alcohol hydroxyl group or thiol group.

In a second aspect of the invention, the sugar structure according to the α-selective glycosylation process in the first aspect of the invention is any one of those (a) to (d) described below.

(a) D-Galactose or L-galactose
(b) D-Gulose or L-gulose
(c) 2-Deoxy-D-galactose or 2-deoxy-L-galactose
(d) Heptose with an essential structure of any one of (a) through (c).

According to the α-selective glycosylation process, the sugar structure as the donor essentially satisfies the given constitutional conditions described in the first aspect. Typical sugar structures satisfying the constitutional conditions are any one of the sugar structures described as (a) to (d) in the second aspect.

In a third aspect of the invention, the sugar structure according to the α-selective glycosylation process in the first or second aspect of the invention takes C1 steric conformation ($^4C_1$ pyranoside structure) when the sugar structure is in the D form or the sugar structure takes 1C steric conformation ($^1C_4$ pyranoside structure) when the sugar structure is in the L form.

Particularly preferably, the sugar structure in the D form as the donor takes C1 steric conformation and the sugar structure in the L form takes 1C steric conformation, because these conformations are preferential conformations, respectively. A possibility cannot be denied however that the sugar structure in the D form taking 1C steric conformation and the sugar structure in the L form taking C1 steric conformation also express the actions and advantages of the first aspect of the invention.

In a fourth aspect of the invention, the protective group in the silyl acetal structure according to the α-selective glycosylation process in any one of the first to third aspects of the invention is dialkylsilylene group.

The protective group in a ring shape as formed over the hydroxyl groups at positions 4 and 6 in the sugar structure can preferably form a dialkylsilylene group, with no specific limitation, as long as the protective group is in the silyl acetal structure.

In a fifth aspect of the invention, the dialkylsilylene group according to the α-selective glycosylation process in the fourth aspect of the invention is di-(t-butyl)-silylene group (DTBS group).

As the dialkylsilylene group, di-(t-butyl)-silylene group (DTBS group) is particularly preferable.

In a sixth aspect of the invention, reactive functional groups except the hydroxyl groups at positions 4 and 6 in the sugar structure are preliminarily treated with protective group modification, before the formation of the protective group in the silyl acetal structure according to the α-selective glycosylation process in any one of the first to fifth aspects of the invention.

The treatment for the modification with given protective groups according to the sixth aspect of the invention effectively suppresses unnecessary side reactions for the formation of the protective group in the silyl acetal structure in the sugar structure or for the subsequent α-selective glycosylation. For adding another sugar and the like to a specific functional group in a sugar or an amino acid or the like as the constitutional part of the donor or the acceptor, further, the functional group is effectively modified with another protective group, which can be eliminated with not any influence on other protective groups.

In a seventh aspect of the invention, the protective group of the amino group for the protective group modification according to the α-selective glycosylation in the sixth aspect of the invention is 2,2,2-trichloroethoxycarbonyl group (Troc group).

In case that the sugar structure contains an amino group (at position 2 in particular), for example in case that the amino group in an amino sugar such as galactosamine and glucosamine is to be protected, phthaloyl group (Phth group) has frequently been used previously. However, Phth group is at such a low introduction efficiency that Phth group is not appropriate for mass-scale synthesis. In case that cyanuric acid and the like concurrently exist in the reaction system, for example, hydrazine is generally used for removing the Phth group. So as to avoid the generation of amides due to the attack thereof to the methyl ester, the methyl ester is once removed. Subsequently, free carboxylic acid is again prepared into methyl ester. Such laborious works for deprotection are essentially required. Concerning these points, the inventors found that protection of amino group with Troc group was suitable from the standpoint of efficient synthesis of α-glycoside.

In an eighth aspect of the invention, the sugar structure for the α-selective glycosylation according to any one of the first to seventh aspects of the invention has a substituent at position 2, the substituent interfering with the α-selective glycosylation through neighboring group participation.

One particular advantage of the actions and advantages of the first aspect of the invention is to secure highly selective α-glycosylation even for such sugar structure with a substituent at position 2, the substituent highly interfering with the α-selective glycosylation through the neighboring group participation during general glycosylation reactions.

In a ninth aspect of the invention, the substituent at position 2 according to the α-selective glycosylation in the eighth aspect is an amino group bound to Troc group or acetyl group.

In case that the substituent at position 2 in the sugar structure is an amino group bound to Troc group or acetyl group (including amino groups modified with Troc group or acetyl group according to the sixth aspect or the seventh aspect), generally, stronger neighboring group participation occurs. As described above, additionally, the neighboring group participation has been a serious disadvantage for the chemical synthesis of glycoproteins of O linkage type. In such case, therefore, the α-selective glycosylation process according to the first aspect is very advantageous.

In a tenth aspect of the invention, use is made of amino acids with alcoholic hydroxyl group or thiol group, and peptide chains, monosaccharides or disaccharides to oligosaccharides or sugar chains containing any one of such amino acids as constituent residues, as the acceptor compounds for the α-selective glycosylation according to any one of the first to ninth aspects of the invention.

Any acceptor compound with alcoholic hydroxyl group or thiol group is satisfactory as the acceptor compound for use in the α-selective glycosylation process, with no specific limitation. Any of the compounds defined in the tenth aspect is preferably listed.

The above and other advantages of the invention will become more apparent in the following description and the accompanying drawings.

DETAILED DESCRIPTION OF THE INVENTION

Modes for carrying out the invention are now described below, including best embodiments of the invention. The term "present invention" simply referred to hereinbelow means the individual inventions in this application.

[α-Selective Glycosylation Process]

The α-selective glycosylation process of the invention is done by a process of glycosylation between a sugar structure (sugar donor) and a compound with alcoholic hydroxyl group or thiol group (sugar acceptor). The characteristic feature thereof includes the ring-shaped formation of a protective group in a silyl acetal structure over hydroxyl groups at positions 4 and 6 in a sugar structure and the subsequent glycosylation between the sugar structure and an acceptor compound. Consequently, so highly α-selective glycosylation process can be progressed that the resulting sugar structure glycoside contains α-glycoside at a ratio of 80% or more in the ratio of α- /β-glycosides.

For forming the protective group in the silyl acetal structure, preferably, given reactive functional groups except the hydroxyl groups at positions 4 and 6 in the sugar structure are preliminarily treated with protective group modification because of the various reasons described in the section of advantages and actions of the eighth aspect of the invention. The types of the reactive functional groups to be preliminarily treated with protective group modification and the positions thereof in the sugar structure are not limited but are appropriately treated with protective group modification on a needed basis. Typically, the amino group or hydroxyl group at position 2 in the sugar structure and the hydroxyl group at position 3 therein are treated with protective group modification.

The protective group for the amino group at position 2 includes for example general acyl-series protective groups such as acetyl group, trihaloacetyl group, levulinoyl group, phthaloyl group and Troc group. The protective group for the hydroxyl group at position 2 includes for example general acyl-series protective groups such as acetyl group, monohaloacetyl group, dihaloacetyl group, levulinoyl group, benzoyl group, and pivaloyl group. The protective group for the hydroxyl group at position 3 includes for example etheric protective groups such as benzyl group, p-methoxybenzyl group and allyl group in addition to acyl-series protective groups such as acetyl group, benzoyl group and pivaloyl group. Among the individual protective groups, many of the protective groups for the amino group or hydroxyl group at position 2 exert strong neighboring group participation in general glycosylation reactions and adversely work for α-selective glycosylation. In the α-selective glycosylation process in accordance with the invention as described above, however, such serious disadvantage never occurs.

[Reaction Conditions and the Like for α-Selective Glycosylation Process]

For the α-selective glycosylation process in accordance with the invention, for example, the reaction conditions, the concentrations of the donor and the acceptor in the reaction system and the use of reaction catalysts are not specifically limited but are appropriately designed if necessary.

Herein, the reaction conditions are preferably as follows. Using a non-polar solvent such as methylene chloride, the glycosylation is done at a reaction temperature within a range of −30° to 0° C. The concentrations of the donor and the acceptor in the reaction system are preferably about 0.1 M. The concentration ratio of the donor and the acceptor in the reaction system is essentially determined in a stoichiometric manner. Preferably, the donor at about 1.5 equivalent moles of the acceptor is used.

[Sugar Structure]

The sugar structure for use in accordance with the invention is a sugar structure of hexose or an aldose having a chain with seven or more carbon atoms in the molecule, the sugar structure containing hydroxyl groups at least at positions 4 and 6 and satisfying the constitutional conditions such that the hydroxyl group at position 4 is in the axial bond and a group at position 5 is in the equatorial bond. The sugar structure may be used as a monosaccharide or as a reducing end of a disaccharide to an oligosaccharide or a sugar chain. As long as the sugar structure satisfies the conditions described above, the type thereof is not specifically limited. However, the sugar structure type typically includes any one of those described below as (a) to (d). Any one of them is described on a concept including derivatives thereof with appropriate substituents introduced at any position, for example derivatives with substituents, such as D/L-galactose with a substituent, for example N-acetylgalactosamine.

(a) D-Galactose or L-galactose
(b) D-Gulose or L-gulose
(c) 2-Deoxy-D-galactose or 2-deoxy-L-galactose
(d) Heptose with an essential structure of any one of (a) through (c).

Based on the reasons described in the section of advantages and actions of the third aspect of the invention, these sugar structures when they are in the D form preferably take a C1 steric conformation of a six-membered ring ($^4C_1$ pyranoside structure) or these sugar structures when they are in the L form preferably take a 1C steric conformation of a six-membered ring ($^1C_4$ pyranoside structure). It cannot be denied that sugar structures never falling under the conditions may possibly be used.

[Formation of Protective Group in Silyl Acetal Structure]

Any protective group in the silyl acetal structure is satisfactory as the ring-shaped protective group formed over the hydroxyl groups at positions 4 and 6 in the sugar structure, with no specific limitation. Dialkylsilylene group is particularly preferably listed. Specifically, di-(t-butyl)-silylene group (DTBS group) is listed preferably. Additionally, for example, di-isopropyl-silylene group, di-isobutyl-silylene group, di-n-butyl-silylene group and di-n-propyl-silylene group are preferably listed.

[Acceptor Compound]

Any organic compound with alcoholic hydroxyl group or thiol group is essentially satisfactory as the acceptor compound for use in accordance with the invention. Preferably, the acceptor compound is an amino acid with alcoholic hydroxyl group or thiol group, for example serine, threonine and cysteine. Because the invention relates to one of organic synthetic processes, it is needless to say that both L-amino acid and D-amino acid can be used.

Further, peptide chains (oligopeptide or polypeptide) containing any one of the amino acids as the constitutional residues are preferably listed as the acceptor compound. Monosaccharides, or disaccharides to oligosaccharides or sugar chains are also preferably listed.

Still further, general organic alcohol compounds or thiol compounds including for example methyl alcohol, ethyl alcohol, and ethyl mercaptan other than those described above, may also be used as the acceptor compounds.

Embodiments

Examples of the invention are described below. These Examples never limit the technical scope of the invention.

EXAMPLE 1

Synthesis of Acceptor Compound

First, the carboxyl group in a sialic acid dimer of the following chemical formula 1 as obtained from colominic acid was prepared into methyl ester, to obtain a sialic acid dimer represented by the following chemical formula 2. In that case, the carboxyl group at its non-reducing end was allowed to form lactone together with the hydroxyl group at position 8 at the reducing end. Further, the acetyl group at the anomeric position in the sialic acid dimer represented by the chemical formula 2 was converted to phenylthio group (SPh group), to obtain disialyl galactose represented by the following chemical formula 3. In the chemical formulas 1 through 3, herein, "Ac" means acetyl group and "Sph" means phenylthio group.

Then, galactose modified with a protective group as shown in the following chemical formula 4 was separately prepared. In the chemical formula 4, "Bn" means benzyl group and "SE" means 2-(trimethylsilyl)ethyl group.

Subsequently, the disialyl galactose represented by the chemical formula 3 was condensed with the galactose represented by the chemical formula 4, under given reaction conditions considered suitable on the basis of the examination of the reaction conditions. The α-isomer represented by the chemical formula 5 below was separated from a mixture of the α- and β-steric isomers thus generated, by silica gel chromatography using a given composition of an eluent. The compound represented by the chemical formula 5 was used as the acceptor compound for use in the α-selective glycosylation process in accordance with the invention.

The α-isomer represented by the chemical formula 5 is 2-(trimethylsilyl)ethyl[methyl 5-acetamide-8-O-(5-acetamide-4,7,8,9-tetra-O-acetyl-3,5-dideoxy-D-glycero-α-D-galacto-2-nonulopyranosilono-1',9-lactone)-4,7-di-O-acetyl-3,5-dideoxy-D-glycero-α-D-galacto-2-nonulopyranosilonate]-(2→3)-2,6-di-O-benzyl-β-D-galactopyranoside.

[Formula 5]

EXAMPLE 2

Synthesis of Sugar Structure

First, a galactosamine triol derivative represented by the following chemical formula 6 was prepared by a predetermined synthetic process, where the hydroxyl group at position 1 was protected with Sph group and the amino group at position 2 was protected with Troc group. The galactosamine triol derivative has the "$^4C_1$" pyranoside structure.

Using DTBS (OTf)$_2$ with trifluoromethanesulfonic acid as an elimination group attached to di-t-butylsilane, then, DTBS was introduced into the positions 4 and 6 in the compound represented by the chemical formula 6 under predetermined reaction conditions, to obtain a compound of the following chemical formula 7, having the protective group in the silyl acetal structure at the positions 4 and 6.

Further, TrocCl reacted with the compound represented by the chemical formula 7 in a pyridine solvent, to obtain a compound represented by the following chemical formula 8, where Troc group was introduced at the position 3. The compound of the chemical formula 8 was used as a sugar structure (galactosamine donor) for use in the α-selective glycosylation process in accordance with the invention.

The compound represented by the chemical formula 8 is phenyl 2-deoxy-4,6-O-di-tert-butylsilylene-1-thio-3-O-(2,2,2-trichloroethoxycarbonyl)-2-(2,2,2-trichloroethoxycarbonylamino)-β-D-galactopyranoside.

[Formula 6]

[Formula 7]

[Formula 8]

EXAMPLE 3

Glycosylation

Figure 3:
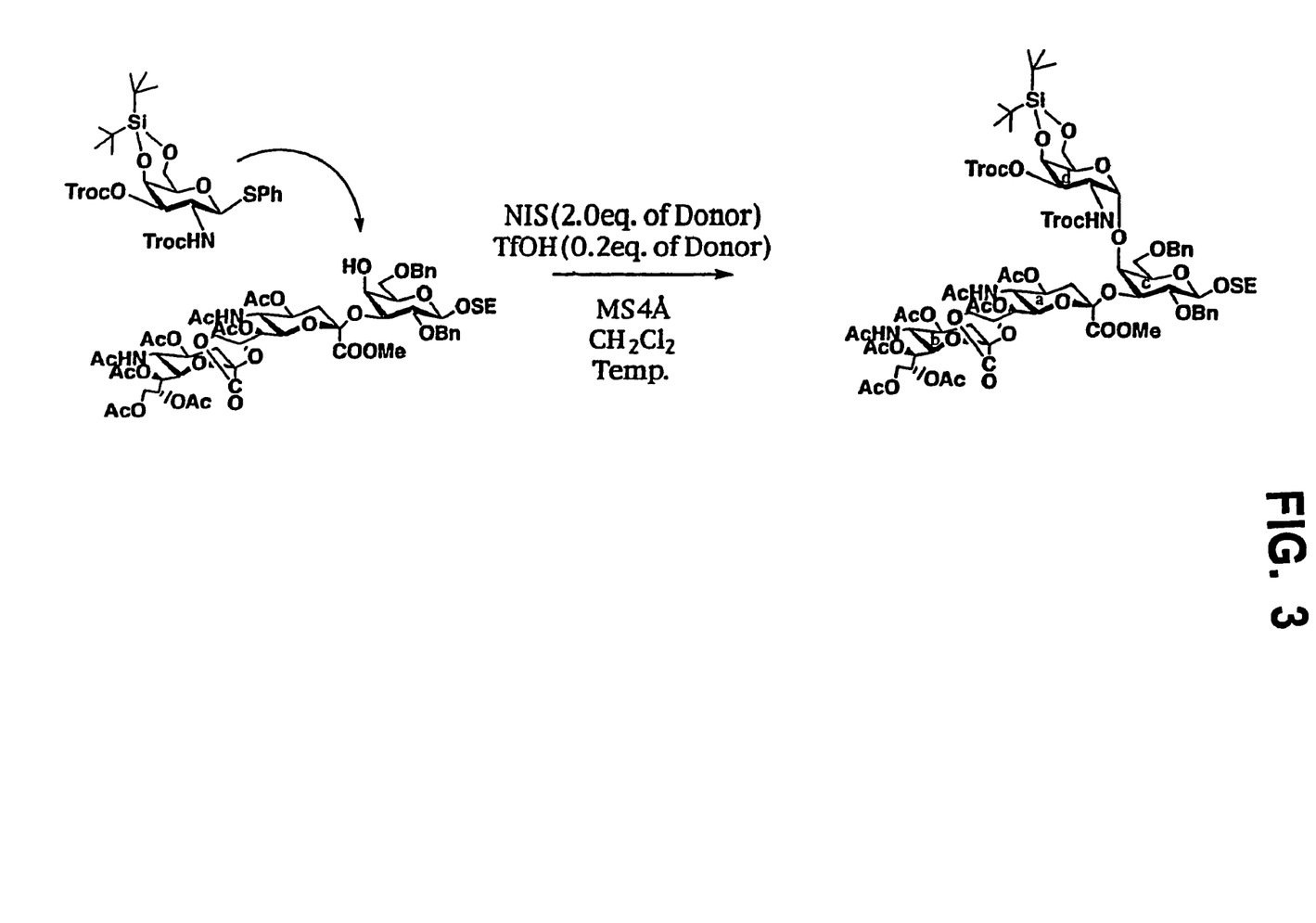
FIG. 3 is a chart depicting the α-selective glycosylation process according to an example of the invention.

As shown in FIG. 3, glycoside represented by the following chemical formula 9 was obtained from the sugar structure of the chemical formula 8 and the acceptor compound of the chemical formula 5, by the process described below.

The glycoside of the chemical formula 9 is 2-(trimethylsilyl)ethyl[methyl 5-acetamide-8-O-(5-acetamide-4,7,8,9-tetra-O-acetyl-3,5-dideoxy-D-glycero-α-D-galadto-2-nonulopyranosilono-1',9-lactone)-4,7-di-O-acetyl-3,5-dideoxy-D-glycero-α-D-galacto-2-nonulopyranosilonate-(2→3)]-[2-deoxy-4,6-O-di-tert-butylsilylene-3-O-(2,2,2-trichloroethoxycarbonyl)-2-(2,2,2-trichloroethoxycarbonylamino)-α-D-galactopyranosyl]-2,6-di-O-benzyl-β-D-galactopyranoside.

[Formula 9]

Specifically, the sugar structure of the chemical formula 8 (118 mg, 0.155 mmol) and the acceptor compound of the chemical formula 5 (100 mg, 77.4 μmol) were dissolved in 5.0 ml of dichloromethane, to which MS4A° (200 mg) was added, for agitation at ambient temperature for one hour. Subsequently, the resulting mixture was cooled to 0° C., to which N-iodosuccinimide (NIS) of 70 mg, i.e. 0.310 mmol and trifluoromethanesulfonic acid (TfOH) of 2.7 μl, i.e. 31.0 μmol were added for agitation.

Under observations of the progress of the reaction by thin-layer chromatography (TLC), the sugar structure of the chemical formula 8 (118 mg), NIS (70 mg) and TfOH (2.7 μl) were again individually added once. In total, the agitation was done for 32 hours.

The termination of the reaction was confirmed by TLC (AcOEt/MeOH=15/1). The generated solids were filtered off through Celite and washed with chloroform. The filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography. Glycoside of the chemical formula 9 (113 mg, 75%) was obtained from the resulting elution solvent.

[Discussions About Examples 1 Through 3]

The Examples 1 through 3 were parts of experiments intended for the purpose of synthetically preparing disialyl-galactose unit. The inventors speculated that because the amino group at position 2 in the sugar structure of the chemical formula 8 was Troc group with possible neighboring group participation, β-glycoside would be obtained from the sugar structure of the chemical formula 8 and the acceptor compound of the chemical formula 5.

However, the resulting glycoside of the chemical formula 9 was unexpectedly α-glycoside according to the analysis by $^1$H-NMR. Not any possible β-glycoside product was confirmed. As shown below in Table 1, additionally, synthetic experiments with the same contents as in Example 3 except for slight modifications of the reaction temperature, the concentrations of the donor and the acceptor and the reaction time were carried out (Example 3 described above corresponds to Entry No. 1 in Table 1). In any of the Examples of such synthetic experiments, only α-glycoside was obtained at yields shown in Table 1, with no confirmation of any product considered as β-glycoside.

TABLE 1

| Entry | Temp. | Conc. | Time | Yield |
|---|---|---|---|---|
| 1 | 0° C. | 46 mM | 32 h | (75%) |
| 2 | 0° C. | 300 mM | 32 h | (68%) |
| 3 | −30° C.→0° C. | 300 mM | 117 h | (70%) |

In the column of yield in Table 1 (the column "Yield"), the numerical figures representing percentage ratios are expressed in parenthesis, because impure signals of possible rotamers are contaminated as observed by $^1$H-NMR. The cause of such phenomenon is not discussed in detail. However, it was suggested that the impure signals emerged due to the influence of the DTBS group.

A novel synthetic approach very simple and advantageous for example for chemical synthesis of sugar chains of O linkage type and the like can be provided, owing to the achievement of the highly selective α-glycosylation process in the synthetic systems as in Examples 1 through 3. The development of an improved potential synthetic process for the chemical synthesis thereof was desired in the past. So as to verify which element enabled the α-selective glycosylation in Examples 1 through 3, the following Examples 4 through 6 and Comparative Example 1 were continuously carried out.

EXAMPLE 4

Change of Acceptor Compound (1)

Using 2-adamantanl (represented by the following chemical formula 10) with less steric hindrance against glycosylation as an acceptor compound, an attempt was made to introduce a sugar structure donor into the hydroxyl group thereof in the following manner.

[Formula 10]

Specifically, the sugar structure of the chemical formula 8 (50 mg, 65.6 μmol) and 2-adamantanol of the chemical formula 10 (30 mg, 0.197 mmol) as an acceptor compound were dissolved in 2.6 ml of dichloromethane, to which MS4A° (80 mg) was added, for agitation at ambient temperature for one hour. Subsequently, the resulting mixture was cooled to 0° C., to which NIS (30 mg, 0.131 mmol) and TfOH (1.2 μl, 13.1 μmol) were added for agitation for one hour.

The termination of the reaction was confirmed by TLC (AcOEt/hexane=1/3). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, glycoside from the condensation was obtained from the resulting elution solvent (AcOEt/hexane=1/20) of the column chromatography. The glycoside was structurally analyzed (by $^1$H-NMR; the same is true hereinbelow). Although β-glycoside was observed at about 8%, α-glycoside was obtained at a yield of 85%.

EXAMPLE 5

Change of Acceptor Compound (2)

For the application of the invention to sugar, an attempt was made to introduce a sugar structure donor into the hydroxyl group at position 6 in a primary alcohol glucose (represented by the chemical formula 11) used as an acceptor compound in the following manner.

[Formula 11]

Specifically, the sugar structure of the chemical formula 8 (50 mg, 65.6 μmol) and the compound of the chemical formula 11 (n-hexyl-2,3,4-tri-O-acetyl-β-D-glucopyranoside; 38 mg, 98.4 μmol) as an acceptor compound were dissolved in 2 ml of dichloromethane, to which MS4A° (100 mg) was added, for agitation at ambient temperature for one hour. Subsequently, the resulting mixture was cooled to 0° C., to which NIS (30 mg, 0.131 mmol) and TfOH (1.2 µl, 13.1 µmol) were added for agitation for 5 hours.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, glycoside from the condensation was obtained from the resulting elution solvent (AcOEt/hexane=¼) of the column chromatography. The glycoside was analyzed structurally. Surprisingly, α-glycoside was obtained at a yield as high as 90%. Some spot of possible β-glycoside was observed on TLC. However, the spot could not be isolated or identified.

EXAMPLE 6

Change of Protective Group at Position 3 in Sugar Structure

So as to demonstrate the influence of a protective group at position 3 in a sugar structure, the compound represented by the chemical formula 12 was used as a sugar structure donor, where Troc group as the protective group at position 3 in the sugar structure of the chemical formula 8 was replaced with acetyl group of the same acyl series. An attempt was made to introduce the sugar structure donor into the hydroxyl group at position 6 in the glucose acceptor of the chemical formula 11 as in Example 5, in the following manner.

[Formula 12]

Specifically, the sugar structure of the chemical formula 12 (50 mg, 79.5 µmol) and the compound of the chemical formula 11 (47 mg, 0.119 mmol) as an acceptor compound were dissolved in 2 ml of dichloromethane, to which MS4A° (100 mg) was added, for agitation at ambient temperature for one hour. Subsequently, the resulting mixture was cooled to 0° C., to which NIS (36 mg, 0.159 mmol) and TfOH (1.4 µl, 15.9 µmol) were added for agitation for 30 minutes.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, the compound represented by the chemical formula 13 was obtained from the resulting elution solvent (AcOEt/hexane=¼) of the column chromatography. The yield was 69 mg, which was almost quantitative at a yield as high as 96%. The result is surprising.

[Formula 13]

COMPARATIVE EXAMPLE 1

Use of Sugar Structure with No Protection with DTBS Group

As a sugar structure donor with no protective group in the silyl acetal structure over the hydroxyl groups at positions 4 and 6 in the sugar structure, the compound represented by the following chemical formula 14 [3,4,6-tri-O-acetyl-2-deoxy-1-thio-2-(2,2,2-trichloroethoxycarbonylamino)-β-D-galactopyranoside] was used. In the following manner, an attempt was made to progress the glycosylation of the sugar structure with an acceptor compound represented by the chemical formula 5.

[Formula 14]

Specifically, the sugar structure of the chemical formula 14 (1.10 g, 1.93 mmol) and the compound of the chemical formula 5 (1.00 g, 0.774 mmol) as an acceptor compound were dissolved in 77 ml of dichloromethane, to which MS4A° (2 g) was added, for agitation at ambient temperature for one hour. Subsequently, the resulting mixture was cooled to 0° C., to which NIS (868 mg, 3.86 mmol) and TfOH (34 µl, 0.386 mmol) were added for agitation for one hour.

The termination of the reaction was confirmed by TLC (AcOEt/MeOH=15/1). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, the glycoside represented by the chemical formula 15 was obtained at a yield of 994 mg and 73% from the resulting elution solvent (AcOEt) of the column chromatography. The glycoside was structurally analyzed. It was found that the glycoside was β-glycoside.

[Formula 15]

[Discussion About Examples 4 Through 6 And Comparative Example 1]

The results of Examples 4 and 5 were discussed together with the results of Example 3. It is determined that the type or chemical structure of the acceptor compound is not an element defining the possibility of α-selective glycosylation. Thus, satisfactorily, the acceptor compound applicable for the α-selective glycosylation in accordance with the invention has an alcoholic hydroxyl group or thiol group as the condition as the acceptor compound for general glycosylation reactions.

The results of Example 6 then indicate that the type of the protective group at position 3 in the sugar structure is not an element defining the possibility of the α-selective glycosylation.

While the total or almost the total amount of the glycosides generated in the individual Examples were α-glycosides, the whole amount of the generated glycosides was β-glycoside, only when a sugar structure donor with no protective group in the silyl acetal structure over the hydroxyl groups at positions 4 and 6 was used as in Comparative Example 1. Therefore, the element defining the possible occurrence of the α-selective glycosylation in accordance with the invention is "the ring-shaped formation of a protective group in a silyl acetal structure over the hydroxyl groups at positions 4 and 6 in a sugar structure donor".

EXAMPLE 7

Neighboring Group Participation of Protective Group at Position 2 in Aminosugar Donor (1)

As described above concerning the related art, the neighboring group participation of the protective group of amino group at position 2 was a serious drawback against the intended α-selective introduction of galactosamine and glucosamine with amino group at position 2 into acceptor compounds. So as to examine whether or not α-selective glycosylation could be progressed even when the Troc group as a protective group of amino group at position 2 in the sugar structure represented by the chemical formula 8 was replaced with a protective group with approved stronger neighboring group participation than the Troc group, therefore, Example 7 was done below.

Using a compound of the following chemical formula 16 as prepared by replacing the Troc group at position 2 in the compound of the chemical formula 8 with Bz group (practi- cally, the Troc group at position 3 was similarly replaced in the same manner) as a sugar structure donor, an attempt was made to introduce the sugar structure donor into the hydroxyl group at position 6 in the glucose acceptor of the chemical formula 11 as in Example 5, in the following manner.

[Formula 16]

Specifically, the sugar structure of the chemical formula 16 (50 mg, 80.5 μmol) and the compound of the chemical formula 11 (47 mg, 0.121 mmol) as an acceptor compound were dissolved in 2 ml of dichloromethane, to which MS4A° (100 mg) was added, for agitation at ambient temperature for one hour. Subsequently, the resulting mixture was cooled to 0° C., to which NIS (36 mg, 0.161 mmol) and TfOH (1.4 μl, 16.1 μmol) were added for agitation for 20 hours.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, the α-glycoside compound represented by the following chemical formula 17 (verified by structural analysis) was obtained from the resulting elution solvent (AcOEt/hexane=⅕) of the column chromatography. The yield was 51 mg at 71%. β-Glycoside was never isolated. Slight amounts of some byproducts were generated.

[Formula 17]

EXAMPLE 8

Neighboring Group Participation of Protective Group at Position 2 in Aminosugar Donor (2)

Due to the same reason as in Example 7, the Troc group as a protective group of the amino group at position 2 in the sugar structure represented by the chemical formula 8 was replaced with Phth group with apparently approved stronger neighboring group participation than the Troc group (Troc group at position 3 was also replaced with acetyl group, actually), to prepare a compound of the following chemical formula 18, which was used as a sugar structure donor for an attempt to introduce the resulting sugar structure donor into the hydroxyl group at position 6 in the glucose acceptor of the chemical formula 11 as in Example 5.

[Formula 18]

The sugar structure of the chemical formula 18 (100 mg, 0.171 mmol) and the compound of the chemical formula 11 (100 mg, 0.256 mmol) as an acceptor compound were dissolved in 4.3 ml of dichloromethane, to which MS4A° (200 mg) was added, for agitation at ambient temperature for one hour. Subsequently, the resulting mixture was cooled to 0° C., to which NIS (77 mg, 0.342 mmol) and TfOH (3 µl, 34.2 µmol) were added for agitation for 30 minutes.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, the α-glycoside compound represented by the chemical formula 19 (confirmed by structural analysis) was obtained from the resulting elution solvent (AcOEt/hexane=⅖) of the column chromatography. The yield was 141 mg at 95%.

[Formula 19]

[Discussion About Examples 7 and 8]

Based on the results of Examples 7 and 8, it was confirmed that the α-selective glycosylation process in accordance with the invention was established with no influence of the intensity of neighboring group participation, which has been a problem in the related art. Thus, it was confirmed that the process was a highly applicable process.

EXAMPLE 9

Synthesis of α-galactosamine-serine

As described above, the highly applicable α-selective glycosylation of the sugar structure donor of galactose type is the chemical synthesis of a sugar chain of O linkage type. In α-galactosamine-L-serine and α-galactosamine-L-threonine composing the peptide linkage site between a sugar chain of O linkage type and a peptide, the latter was selected for an attempt of the α-selective glycosylation process, as described below.

First, a sugar structure of the chemical formula 8 and with introduced Troc group at position 3 was used, taking account of subsequent extension of the sugar chain. Concerning the serine side, two types of protective groups introduced therein as represented by the chemical formulas 20 and 21 were prepared, taking account of subsequent extension of the peptide chain. As described below in Examples 9-1 and 9-2, some difference in yield was observed, depending on the difference in the protective groups of the amino acid. In any of the cases, high α-selectivity was expressed as expected.

[Formula 20]

[Formula 21]

EXAMPLE 9-1

The sugar structure of the chemical formula 8 (122 mg, 0.160 mmol) and the compound of the chemical formula 20 (N-benzyloxycarbonyl-L-serine-pentafluorophenyl ester; 50 mg, 0.123 mmol) as an acceptor compound were dissolved in 2.8 ml of dichloromethane, to which MS4A° (170 mg) was added, for agitation at ambient temperature for one hour. Subsequently, the resulting mixture was cooled to 0° C., to which NIS (72 mg, 0.320 mmol) and TfOH (2.8 µl, 32.0 µmol) were added for agitation for 30 minutes.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat: $Na_2CO_3$, sat. $Na_2S_2O_3$, and brine, dried and concentrated over $Na_2SO_4$. The resulting syrup was subjected to column chromatography.

Then, the expected α-glycoside, i.e. α-galactosamine-serine (confirmed by structural analysis) was obtained from the resulting elution solvent (AcOEt/hexane=⅓) of the column chromatography. The yield was 117 mg at 90%.

EXAMPLE 9-2

The sugar structure of the chemical formula 8 (100 mg, 0.131 mmol) and the compound of the chemical formula 21 (N-9-fluorenylmethoxycarbonyl-L-serine-pentafluorophenyl ester; 50 mg, 0.101 mmol) as an acceptor compound were dissolved in 2.3 ml of dichloromethane, to which MS4A° (150 mg) was added, for agitation at ambient temperature for one hour. Subsequently, the resulting mixture was cooled to 0° C., to which NIS (59 mg, 0.262 mmol) and TfOH (2.3 µl, 26.2 µmol) were added for agitation for 30 minutes.

The termination of the reaction was confirmed by TLC (AcOEt/hexane=½). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography.

Then, the expected α-glycoside, i.e. α-galactosamine-serine (confirmed by structural analysis) was obtained from the resulting elution solvent (AcOEt/hexane=⅓) of the column chromatography. The yield was 91 mg at 78%.

EXAMPLE 10

Change of Protective Group at Position 1 in Sugar Structure

Using sugar structures prepared by individually replacing the protective group (Sph group) of the hydroxyl group at position 1 in the sugar structure of the chemical formula 8 with $SCH_3$ group (I), F group (Ro) and $OC(NH)CCl_3$ group (Ha), an α-selective glycosylation process between one of the resulting sugar structures and 2-adamantanol was progressed.

EXAMPLE 10-1

The sugar structure (I) (150 mg, 0.214 mmol) and 2-adamantanol (21.7 mg, 0.143 mmol) were dissolved in 3.5 ml of dichloromethane under argon purging, to which MS4A° (170 mg) was added, for agitation at ambient temperature for one hour. Subsequently, the resulting mixture was cooled to 0° C., to which NIS (96.4 mg, 0.428 mmol) and TfOH (3.8 µl, 42.8 µmol) were added for agitation for 30 minutes.

The termination of the reaction was confirmed by TLC (AcOEt/hexane=⅓). The generated solids were filtered off through Celite and washed with chloroform. Further, the filtrate and the washing solution were combined together and diluted with chloroform. The organic layer was rinsed sequentially with sat. $Na_2CO_3$, sat. $Na_2S_2O_3$, and brine, dried and concentrated over $Na_2SO_4$. The resulting syrup was subjected to column chromatography. Then, the glycoside obtained from the resulting elution solvent (AcOEt/hexane=1/30) was analyzed structurally. Although β-glycoside was observed at about 11% (13 mg), α-glycoside was obtained at a yield of 85% (106 mg).

EXAMPLE 10-2

The sugar structure (Ro) (150 mg, 0.223 mmol) and 2-adamantanol (22.6 mg, 0.148 mmol) were dissolved in 3.7 ml of dichloromethane under argon purging, to which MS4A° (170 mg) was added, for agitation at ambient temperature for one hour. Subsequently, the resulting mixture was cooled to 0° C., to which $SnCl_2$ (42.3 mg, 0.223 mmol) and $AgClO_4$ (55.5 mg, 0.267 mmol) were added in darkness for agitation for 16 hours.

The termination of the reaction was confirmed by TLC (AcOEt/hexane=¼). The generated solids were filtered off through Celite and washed with chloroform. Further, the filtrate and the washing solution were combined together and diluted with chloroform. The organic layer was rinsed sequentially with sat. $NaHCO_3$, and brine, dried and concentrated over $Na_2SO_4$. The resulting syrup was subjected to silica gel column chromatography. Then, the glycoside obtained from the resulting elution solvent (AcOEt/hexane=1/30) was analyzed structurally. Although β-glycoside was observed at about 10% (12 mg), α-glycoside was obtained at a yield of 78% (93 mg).

EXAMPLE 10-3

The sugar structure (Ha) (150 mg, 0.184 mmol) and 2-adamantanol (18.7 mg, 0.123 mmol) were dissolved in 3.1 ml of dichloromethane in argon purging, to which AW-300 (170 mg) was added, for agitation at ambient temperature for one hour. Subsequently, the resulting mixture was cooled to 0° C., to which TMSOf (0.670 µl, 3.68 µmol) was added for agitation for 30 minutes.

The termination of the reaction was confirmed by TLC (AcOEt/hexane=⅓). The generated solids were filtered off through Celite and washed with chloroform. Further, the filtrate and the washing solution were combined together and diluted with chloroform. The organic layer was rinsed sequentially with sat. $NaHCO_3$, and brine, dried and concentrated over $Na_2SO_4$. The resulting syrup was subjected to silica gel column chromatography. Then, the glycoside obtained from the resulting elution solvent (AcOEt/hexane=1/30) was analyzed structurally. Although β-glycoside was observed at about 9% (9 mg), α-glycoside was obtained at a yield of 87% (86 mg).

While the preferred embodiments have been described, variations thereto will occur to those skilled in the art within the scope of the present inventive concepts, which are delineated by the following claims.

The invention claimed is:

1. An α-selective glycosylation process between a donor compound having a sugar structure and an acceptor compound having an alcoholic hydroxyl group or thiol group comprising, (1) the step of providing a sugar structure of hexose or an aldose having a chain with six carbon atoms in the molecule which is a monosaccharide or a reducing end of an oligosaccharide having two or more monosaccharide residues or a sugar chain, which sugar structure satisfies the constitutional conditions such that the sugar structure has hydroxyl groups at positions 4 and 6 and that the hydroxyl group at position 4 is in an axial bond and a group at position 5 is in equatorial bond, wherein the sugar structure is substituted with amino at position 2, the amino being bound to a 2,2,2-trichloroethoxycarbonyl group, the sugar structure having a hydroxyl group at the 3-position that is protected with a group selected from among an acetyl group, a benzoyl group, a pivaloyl group, a benzyl group, a p-methoxybenzyl group and an allyl group, (2) a step of forming a protective group in a silyl acetal structure in a ring shape over the hydroxyl groups at positions 4 and 6 in the sugar structure, and (3) a step of promoting the glycosylation between the sugar structure and the alcoholic hydroxyl groups or thiol group of the acceptor compound, and (4) a step of preparing a sugar structure glycoside containing α-glycoside at a ratio of 80% or more in the ratio of α-/β-glycosides, wherein
the acceptor compound is selected from the group consisting of serine, threonine, cystine, peptides, mono or oligogalactopyranosides, and mono or oligoglucopyranosides.

2. An α-selective glycosylation process according to claim 1, where the protective group in the silyl acetal structure is a dialkylsilylene group.

3. An α-selective glycosylation process according to claim 2, where the dialkylsilylene group is di-(t-butyl)-silylene group (DTBS group).

4. An α-selective glycosylation process according to claim 2, where the dialkylsilylene group is di-isopropyl-silylene group, di-isobutyl-silylene group, di-n-butyl-silylene group or di-n-propyl-silylene group.

5. An α-selective glycosylation process according to claim 1, where reactive functional groups except the hydroxyl group at positions 4 and 6 in the sugar structure are preliminarily treated with protective group modification before the formation of the protective group silylacetal structure.

6. A process for glycosylation of a glycosylation acceptor having an alcoholic hydroxyl group or a thiol group with a glycosylation donor, wherein
the glycosylation donor comprises a pyranoside structure, derivable from an aldose having six carbon atoms, having an equatorially-positionable hydroxyl group at the 4-position of the pyranoside structure, an axially-positionable hydroxymethyl or hydroxymethylene group at the 5-position of the pyranoside structure, and amino at the 2-position of the pyranoside structure, the amino being bound to a 2,2,2-trichloroethoxycarbonyl group, the pyranoside structure having a hydroxyl group at the 3-position that is protected with a group selected from among an acetyl group, a benzoyl group, a pivaloyl group, a benzyl group, a p-methoxybenzyl group and an allyl group, and further wherein
the glycosylation donor is a monosaccharide, a disaccharide, or an oligosaccharide, the α-selective glycosylation process comprising the steps of
a) forming a cyclic silyl acetal group bridging the equatorially-positionable hydroxy group at the 4-position of the pyranoside structure and the hydroxyl group of the axially-positionable hydroxymethyl or hydroxymethylene group at the 5-position of the pyranoside structure so as to form a bicyclo [6.6.0.] structure, and
b) glycosylating the alcoholic hydroxyl group or thiol group of the glycosylation acceptor to form glycosylated product, whereby the ratio of α-glycosylated product to β-glycosylated product is at 4:1.

7. The process of claim 6 wherein the pyranoside structure is selected from the group consisting of glucopyranoside, galactopyranoside, 2-amino-2-deoxyglucopyranoside, and 2-amino-2-deoxygalactopyranoside.

8. The process of claim 6 wherein the glycosylation acceptor comprises a glycoside moiety having an alcoholic hydroxyl group at its 6-position.

9. The process of claim 6 wherein the glycosylation acceptor is selected from the group consisting of: galactopyranosides having a hydroxyl group at the 4-position, glucopyranosides having a hydroxyl group at the 6- position, serine, threonine, and cysteine.

10. The process of claim 9 wherein the pyranoside structure is selected from the group consisting of glucopyranoside, galactopyranoside, 2-amino-2-deoxyglucopyranoside, and 2-amino-2-deoxygalactopyranoside.

11. An α-selective glycosylation process comprising promoting glycosylation between a sugar structure and an acceptor compound, wherein the sugar structure is substituted with amino at position 2, the amino being bound to a 2,2,2-trichloroethoxycarbonyl group, the sugar structure having hydroxyl groups at positions 4 and 6, and having a protective group of a silyl acetal structure in a ring shape over the hydroxyl groups at positions 4 and 6.

12. The α-selective glycosylation process of claim 11 wherein the sugar structure is hexose or an aldose having a chain with six carbon atoms and the acceptor compound has an alcoholic hydroxyl group or thiol group, the sugar structure being a monosaccharide or a reducing end of an oligosaccharide having two or more monosaccharide residues or a sugar chain, the hydroxyl group at position 4 being in an axial bond and a group at positon 5 being in an equatorial bond, the sugar structure having a hydroxyl group at the 3-position that is protected with a group selected from among an acteyl group, a benzoyl group, a pivaloyl group, a benzyl group, a p-methoxybenzyl group and an allyl group.

13. The α-selective glycosylation process of claim 11 wherein the acceptor compound is selected from the group consisting of serine, threonine, cystine, peptides, mono- or oligogalactopyranosides, and mono or oligoglucopyranosides.

14. The α-selective glycosylation process of claim 12 wherein the acceptor compound is selected from the group consisting of serine, threonine, cystine, peptides, mono- or oligogalactopyranosides, and mono or oligoglucopyranosides.

15. The α-selective glycosylation process according to claim 11, where the protective group of the silyl acetal structure is a dialkylsilylene group.

16. The α-selective glycosylation process according to claim 15, where the dialkylsilylene group is di-(t-butyl)-silylene group (DTBS group).

17. The α-selective glycosylation process according to claim 15, where the dialkylsilylene group is di-isopropyl-silylene group, di-isobutyl-silylene group, di-n-butyl-silylene group or di-n-propyl-silylene group.

18. The α-selective glycosylation process according to claim 11, where reactive functional groups except the hydroxyl groups at positions 4 and 6 in the sugar structure are preliminarily treated with protective group modification before the formation of the protective group in the silyl acetal structure.

19. A process for the glycosylation of a glycosylation acceptor comprising promoting the glycosylation between a glycosylation donor comprising a pyranoside structure and a glycosylation acceptor, wherein the pyranoside structure is substituted with amino at the 2-position that is bound to a 2,2,2-trichloroethoxycarhonyl group, and having a cyclic silyl acetal group bridging an equatorially-positionable hydroxy group at 4-position of the pyranoside structure and a hydroxyl group of the axially-positionable hydroxymethyl or hydroxymethylene group at the 5-position of the pyranoside structure so as to form a bicyclo [6.6.0.] structure.

20. The process for the glycosylation of a glycosylation acceptor of claim 19 wherein the pyranoside structure is derivable from an aldose having six carbon atoms, the pyranoside structure having an equatorially-positionable hydroxyl group at the 4-position, an axially-positionable hydroxymethyl or hydroxymethylene group at the 5-position, a hydroxyl group at the 3-position protected with a group selected from among an acetyl group, a benzoyl group, a pivaloyl group, a benzyl group, a p-methoxybenzyl group and an allyl group, and further wherein the glycosylation donor is a monosaccharide, a disaccharide, or an oligosaccharide.

21. The process for the glycosylation of a glycosylation acceptor of claim 20 further comprising glycosylating the alcoholic hydroxyl group or thiol group of the glycosylation acceptor to form glycosylated product.

22. The process of claim 19 wherein the pyranoside structure is selected from the group consisting of glucopyranoside, galactopyranoside, 2-amino-2-deoxyglucopyranoside, and 2-amino-2-deoxygalactopyranoside.

23. The process of claim 19 wherein the glycosylation acceptor comprises a glycoside moiety having an alcoholic hydroxyl group at its 6-position.

24. The process of claim 19 wherein the glycosylation acceptor is selected from the group consisting of galactopyranosides having a hydroxyl group at the 4-position, glucopyranosides having a hydroxyl group at the 6-position, serine, threonine, and cysteine.

25. The process of claim 19 wherein the pyranoside structure is selected from the group consisting glucopyranoside, galactopyranoside, 2 amino-2 -deoxyglucopyranoside, and 2-amino-2-deoxygalactopyranoside.

\* \* \* \* \*